US008354245B2

(12) United States Patent
Piasio et al.

(10) Patent No.: US 8,354,245 B2
(45) Date of Patent: Jan. 15, 2013

(54) METHOD OF ASSAYING GLUCOSE-6-PHOSPHATE DEHYDROGENASE ON A CHROMATOGRAPHIC TEST STRIP

(75) Inventors: Roger N. Piasio, Cumberland Foreside, ME (US); Nathan Turner, Portland, ME (US)

(73) Assignee: Alere Scarborough, Inc., Scarborough, ME (US)

( * ) Notice: Subject to any disclaimer, the term of this patent is extended or adjusted under 35 U.S.C. 154(b) by 0 days.

(21) Appl. No.: 12/211,304

(22) Filed: Sep. 16, 2008

(65) Prior Publication Data

US 2009/0011436 A1    Jan. 8, 2009

Related U.S. Application Data

(60) Division of application No. 10/784,155, filed on Feb. 24, 2004, now Pat. No. 7,425,302, which is a continuation-in-part of application No. 10/370,574, filed on Feb. 24, 2003, now abandoned.

(51) Int. Cl.
*C12Q 1/32* (2006.01)
(52) U.S. Cl. ............... 435/26; 422/56; 422/60
(58) Field of Classification Search ........ 435/4; 422/56, 422/60
See application file for complete search history.

(56) References Cited

U.S. PATENT DOCUMENTS

| | | | |
|---|---|---|---|
| 3,791,574 A | 2/1974 | Picquot | |
| 3,791,933 A | 2/1974 | Moyer et al. | |
| 5,290,683 A | 3/1994 | Israel et al. | |
| 5,409,664 A * | 4/1995 | Allen | 422/56 |
| 5,527,509 A | 6/1996 | Gibson et al. | |
| 5,554,531 A | 9/1996 | Zweig | |
| 5,939,252 A * | 8/1999 | Lennon et al. | 435/4 |
| 5,945,345 A * | 8/1999 | Blatt et al. | 436/518 |
| 6,017,767 A | 1/2000 | Chandler et al. | |
| 6,306,642 B1 | 10/2001 | Nelson et al. | |
| 6,551,842 B1 * | 4/2003 | Carpenter | 436/518 |
| 6,649,418 B1 | 11/2003 | Geisberg | |
| 6,663,833 B1 | 12/2003 | Stave et al. | |
| 6,737,277 B1 * | 5/2004 | Kang et al. | 436/514 |
| 6,766,817 B2 | 7/2004 | da Silva et al. | |
| 7,425,302 B2 * | 9/2008 | Piasio et al. | 422/56 |
| 2003/0032196 A1 | 2/2003 | Zhou | |
| 2004/0156037 A1 | 8/2004 | Mawhirt et al. | |

FOREIGN PATENT DOCUMENTS

| | | | |
|---|---|---|---|
| CN | 1261670 A | | 8/2000 |
| EP | 291194 A1 | | 11/1988 |
| EP | 0441325 A2 | | 8/1991 |
| EP | 0 0990 706 | * | 4/2000 |
| EP | 0990706 A1 | | 4/2000 |
| WO | WO-0062060 A2 | | 10/2000 |
| WO | WO-0079276 A1 | | 12/2000 |
| WO | WO-03/062824 | | 7/2003 |

OTHER PUBLICATIONS

Office Action issued for U.S. Appl. No. 10/784,155, filed Feb. 24, 2004, mailed from the U.S. Patent and Trademark Office on May 17, 2007.
Office Action issued for U.S. Appl. No. 10/784,155, filed Feb. 24, 2004, mailed from the U.S. Patent and Trademark Office on Oct. 19, 2007.
Office Action issued for U.S. Appl. No. 10/784,155, filed Feb. 24, 2004, mailed from the U.S. Patent and Trademark Office on Jan. 14, 2008.
Notice of Allowance issued for U.S. Appl. No. 10/784,155, filed Feb. 24, 2004, mailed from the U.S. Patent and Trademark Office on Jun. 3, 2008.
Office Action issued for U.S. Appl. No. 10/784,155, filed Feb. 24, 2004, mailed from the U.S. Patent and Trademark Office on Dec. 19, 2006.
Office Action issued for Application No. 2006-503810 filed on Feb. 24, 2004, mailed from the Japan Patent Office on Dec. 28, 2009.
Office Action issued for Application No. 2004216189 filed on Feb. 24, 2004, mailed from the Australian Patent Office on Aug. 1, 2008.
Office Action issued for Application No. 200480006045 filed on Feb. 24, 2004, mailed from the Chinese Patent Office on Jan. 12, 2007.
Office Action issued for Application No. 200480006045 filed on Feb. 24, 2004, mailed from the Chinese Patent Office on Jan. 4, 2008.
Office Action issued for Application No. 200480006045 filed on Feb. 24, 2004, mailed from the Chinese Patent Office on Jun. 19, 2009.
Office Action issued for U.S. Appl. No. 10/370,574, filed Feb. 24, 2003, mailed from the U.S. Patent and Trademark Office on Sep. 5, 2006.
Notice of Grant of Patent Right for Invention issued for Application No. 200480006045, mailed from the Chinese Patent Office on Jan. 15, 2010.
Notice of Acceptance issued for Application No. 2004216189, mailed from the Australian Patent Office on Nov. 30, 2009.
Office Action for Canadian Application No. 2,516,546 dated May 10, 2011.
Supplementary European Search Report for EP 04714110 dated Nov. 18, 2011.
Office Action for European Application No. 04 714 110.6 dated Jun. 20, 2012.

* cited by examiner

*Primary Examiner* — Ralph Gitomer
(74) *Attorney, Agent, or Firm* — Foley Hoag LLP

(57) ABSTRACT

A lateral flow chromatographic assay format for the performance of rapid enzyme-driven assays is described. A combination of components necessary to elicit a specific enzyme reaction, which are either absent from the intended sample or insufficiently present therein to permit completion of the desired reaction, are predeposited as substrate in dry form together with ingredients necessary to produce a desired color upon occurrence of the desired reaction. The strip is equipped with a sample pad placed ahead of the substrate deposit in the flowstream, to which liquid sample is applied. The sample flows from the sample pad into the substrate zone where it immediately reconstitutes the dried ingredients while also intimately mixing with them and reacting with them at the fluid front. The fluid front moves rapidly into the final "read zone" wherein the color developed is read against predetermined color standards for the desired reaction. Pretreatment pads for the sample, as needed, (e.g. a lysing pad for lysing red blood cells in whole blood) are placed in front of the sample pad in the flow path as appropriate. The assay in the format of the invention is faster and easier to perform than analogous wet chemistry assays.

5 Claims, 4 Drawing Sheets

FIG.1A
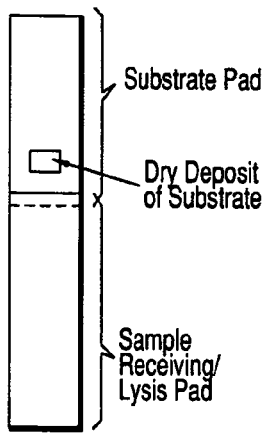
FIG.1B
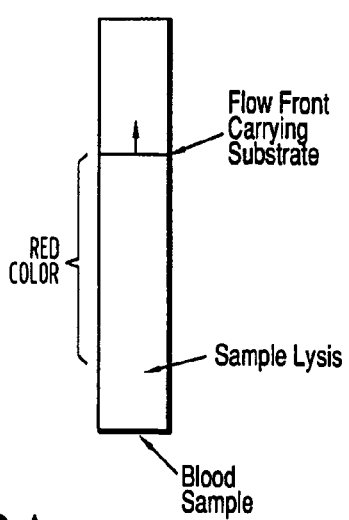
FIG.1C
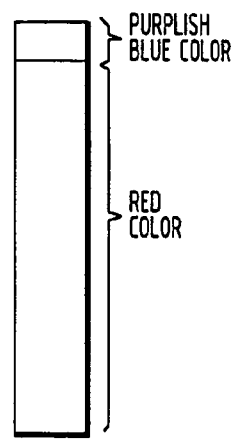
FIG.2A
| Activity Level (U/dl) | Time to Purple (sec) |
|---|---|
| 94.5 | 30 |
| 72.4 | 40 |
| 36.2 | 90 |
| 18.1 | 180 |
FIG.2B
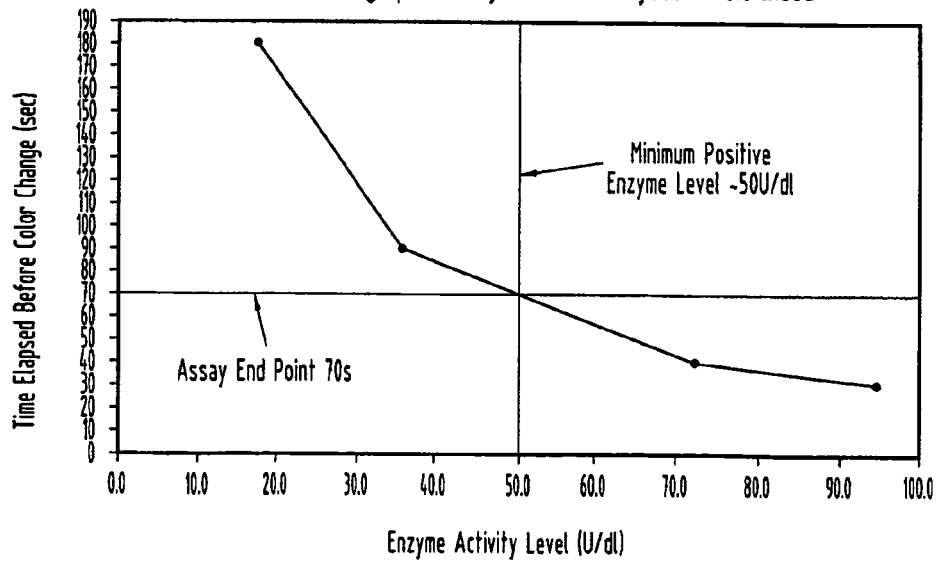

Figure 3A
| Cholesterol Level (mg/dl) | Time to Visualization (sec) | Interpolated Cholesterol (mg/dl) | Error |
|---|---|---|---|
| 400 | 20 | 382.6 | -4.3% |
| 200 | 30 | 202.9 | 1.5% |
| 100 | 45 | 107.6 | 7.6% |
| 38 | 90 | 36.4 | -4.3% |
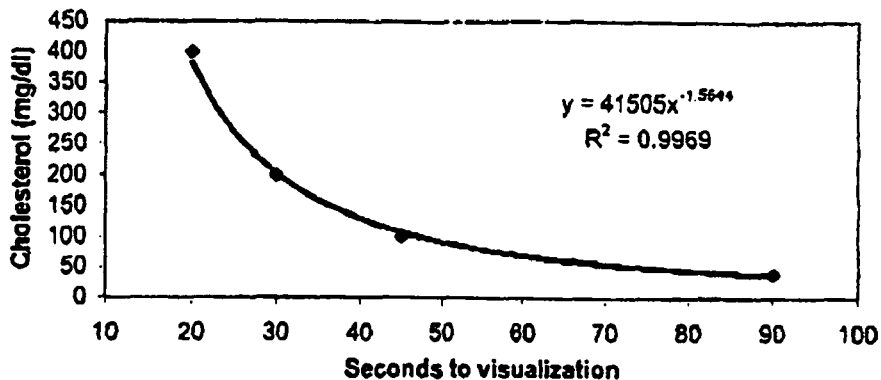
Figure 3B
Figure 4A
| Cholesterol Level (mg/dl) | Time to Visualization (sec) | Interpolated Cholesterol (mg/dl) | Error |
|---|---|---|---|
| 327.6 | 145 | 312.1 | -4.7% |
| 167.6 | 205 | 180.1 | 7.4% |
| 87.6 | 325 | 86.6 | -1.1% |
| 38 | 550 | 37.6 | -1.2% |
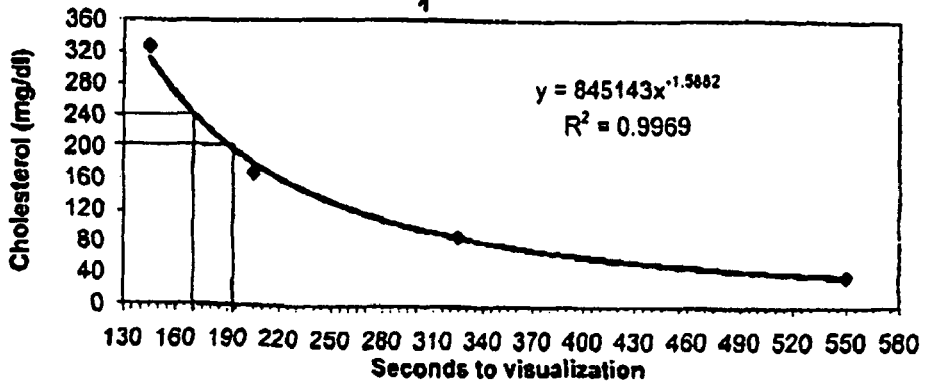
Figure 4B Figure 5A
| β-Lactamase Activity (U/ml) | Time to Visualization (sec) | Interpolated Activity (U/ml) | Error |
|---|---|---|---|
| 0.01 | 1 | 0.0101 | 1.0% |
| 0.005 | 30 | 0.0047 | -6.8% |
| 0.002 | 120 | 0.0024 | 22.0% |
| 0.001 | 300 | 0.0010 | -2.6% |
Figure 5B
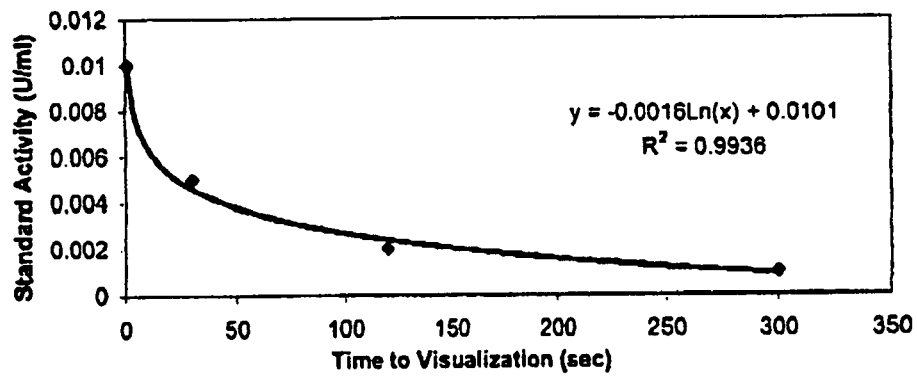
Figure 6A
| E.Coli Concentration (Cells/ml) | Time to Visualization (sec) |
|---|---|
| 9.27E+07 | 60 |
| 9.27E+06 | 600 |
| 4.64E+06 | 1200 |
Figure 6B
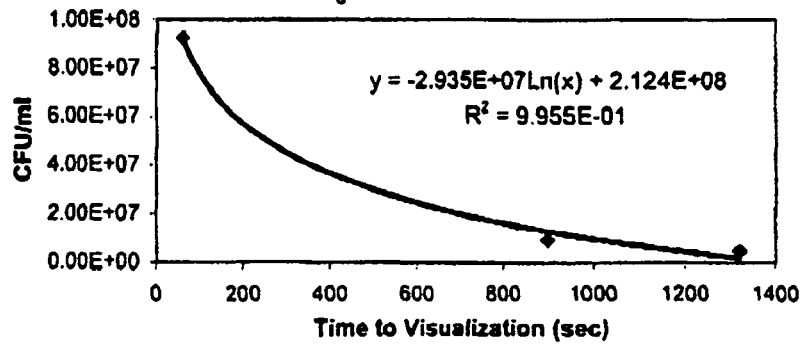

Figure 7

| Peroxidase activity (U/dl) | Time to Visualization (min) |
|---|---|
| 20 | 1 |
| 5 | 5 |
| 1 | 15 |
| 0 | >30min |

METHOD OF ASSAYING GLUCOSE-6-PHOSPHATE DEHYDROGENASE ON A CHROMATOGRAPHIC TEST STRIP

RELATED APPLICATIONS

This application is a Divisional application of U.S. application Ser. No. 10/784,155, filed Feb. 24, 2004 now U.S. Pat. No. 7,425,302, which is a Continuation-in-part of U.S. application Ser. No. 10/370,574 filed Feb. 24, 2003 now abandoned. These applications are incorporated herein by reference in their entireties.

INTRODUCTION

The present invention relates to conducting rapid, dry-chemistry, enzyme-driven chemistry assays using lateral flow chromatography.

BACKGROUND OF THIS INVENTION

The human enzyme glucose-6-phosphate dehydrogenase ("G6PD") performs a critical function in human biochemistry. It is part of the oxidative pentose pathway, wherein it functions to minimize oxidative attacks of free radicals upon cells by providing reducing equivalents—i.e., G6PD converts glucose-6-phosphate to 6-phosphoglutonate, thereby liberating a proton that reduces nicotinamide adenine dinucleotide phosphate, NAPD, to NAPDH. The NAPDH initiates a series of downstream reactions that ultimately reduce the free radical oxidizing agents and render many of them ineffective in normal human biochemistry.

G6PD is present in all human cells, but it is in higher concentration in red blood cells which, in one of their primary functions, act as oxygen transport vehicles and are hence particularly susceptible to oxidative attack. The efficiency of the G6PD system is remarkably high as reflected by the fact that during normal activity less than 1% of its capacity is utilized in combating and preventing undesirable oxidative effects. However, when strong oxidizing agents, such as members of the quinine class of anti-malarial drugs must be introduced to humans, the need for rapid production of reducing agents is greatly increased.

Several mutations of the gene which encodes for G6PD are known which decrease the efficiency of the enzymes in the biochemistry of individuals processing such a mutation in both halves of their genome, causing the quantity of their G6PD to remain at the same level as in people with a normal gene, but also causing their G6PD to show greatly reduced specific activity. In these individuals, administration of strong oxidizing agents such as members of the class of quinine-type anti-malarials, may cause severe clinical complications, such as hemolytic anemia, because the low specific activity of their G6DP does not enable the production of sufficient reducing agents to prevent rapid unwanted oxidative effects on their red blood cells. In areas where malarial infections are common and at times even epidemic, a need therefore exists for a rapid efficient test that will readily distinguish persons having G6PD of low specific activity from persons whose G6PD activity is normal and will enable medical personnel to ensure that (1) the quinine antimalarials are prescribed only for individuals with normal or better G6PD specific activity and (2) persons with lower than normal G6PD activity are medicated with an alternative type of anti-malarial drugs.

Heretofore, assays that involve enzyme activity, in any context, have most usually been conducted in "wet chemistry" formats which require trained laboratory personnel to prepare for and perform them. The reagents for such assays must either be made fresh from dry components or be reconstituted from commercially available dried formulations. Wet reagents are less stable than dried ingredients or dried formulations and, to the extent they must be stored, more stringent, carefully monitored storage conditions, including special handling techniques to prevent contamination, are required. Those assays also require instruments such as spectrophotometers, fluorimeters or other such instrumental equipment to read the endpoint results of the assay. Such assays are not practical for use in doctor's offices, hospitals and nursing home facilities, under epidemic conditions, or for home or field use.

Automated clinical chemistry analyzer systems are in industrial use which perform dry chemistry formatted assays wherein the presence, absence, concentration or specific activity of a substance present in or absent from a sample is determined. Such a substance is, for purpose of this application, referred to as the "analyte" and it may be an enzyme per se (as in the G6PD assay hereinafter described in detail) or a substance necessary to the elicitation of a specific enzyme activity. Examples of automated clinical chemistry analyzer systems are the Johnson and Johnson Vitros™ and the Roche Cobas™ systems. These and similar automated systems are not subject, when performing as designed, to the preparation skill requirements and shelf life problems associated with humanly performed dry chemistry assay work. Because programmed robots perform the manipulative tasks, the need for intensively trained humans is likewise avoided. The systems, however, require on board reader instrumentation and they are necessarily too large, too complicated and generally too burdened with infrastructure requirements to be practical for use in doctor's offices or homes and in many hospitals, clinics and like places. Clearly, they have too many technical requirements for field use.

There are available, as well, a very few non-instrument based dry-chemistry assays, such as the Orasure QED™ assay for alcohol which is based upon use of the alcohol dehydrogenase enzyme to determine alcohol content of saliva in the field. This and other known assays of this genre have heretofore been limited to determinations that can be made on samples that are free of substances that may obscure, inhibit or in some other manner intrinsically interfere with and render imprecise determinations that are dependent upon some aspect of enzymatic action or content.

An example of an enzymatic assay that operates on samples containing visually obscuring substances and uses antibody capture zones to select for enzyme analytes is shown in U.S. Pat. No. 5,506,114. This system requires wash steps to remove the visually obscuring substances and is sufficiently cumbersome to perform that it is impractical for field use or use in doctor's offices, homes, most clinics and many hospitals and the like.

BRIEF DESCRIPTION OF THE INVENTION

In its broadest aspect, this invention rests upon the recognition that rapid, dry chemistry, enzyme-driven assays may advantageously be conducted using lateral flow chromatography, wherein predeposited dry substrate, as hereinafter defined, is reconstituted chromatographically by the lateral flow of liquid sample and entrained substrate through at least one region of a lateral flow device, with production of a calorimetric reaction at the forward flow front of the sample-substrate mixture in the endpoint or "read" zone of the chromatographic device. The color produced is that typical of the endpoint color of the corresponding wet chemistry clinical assay, obtained in the region of the device where forward flow ceases, i.e., the zone that is farthest from the point of sample introduction. It is within the scope of the invention, depending upon the specific assay being conducted, to include chromatographic regions in the device that remove interfering substances present in the sample and/or regions that have been treated to preconcentrate the analyte before it moves into the endpoint reaction zone. In some assays, at least one substance heretofore deemed to interfere with the endpoint observation, i.e., hemoglobin, need not be removed since its otherwise endpoint-obscuring color deposits equally in the endpoint zone and the zone just preceding it. The result in this case is that the endpoint is easily observable by direct comparison of the color produced in the endpoint zone with that of the unreacted red color in the abutting, immediately preceding zone.

In general, in the lateral chromatography, enzyme-driven assays of this invention, the movable, predeposited dry substrate is placed near to and just beyond the junction of the sample receiving pad and the next pad in the sample flow path on the chromatographic strip. It may, however be placed elsewhere in the sample flow path to accommodate particular requirements of either the sample or one or more ingredients in the substrate, so long as it is placed in the flow path substantially before the endpoint, or "read", zone where sample flow stops and any excess fluid present runs off into an absorption pad or other sink device that may be provided.

It is important that the dried substrate be deposited within a tightly confined area so as to facilitate its being completely picked up by the forward flow of the sample. The placement in the flow path of the dried substrate should also take into consideration that reconstitution of the substrate in dissolved or dispersed form within the liquid sample is desirably completed by the time the sample reaches the point where sample flow ceases.

It has also been found that the present enzyme-driven lateral flow assay can be combined with known solid phase isolation methods, and that in at least some instances when this is done, the sensitivity of detection of the desired end point is enhanced substantially.

The format of such methodology involves binding a ligand for the target enzyme to a particulate solid support material—e.g., disks of filter paper or other common solid support material, such as but not limited to nitrocellulose, nylon, polyethylene, etc. or superparamagnetic particles and the like—by coupling, coating, impregnation or any other known method. The ligand-bound particles are then mixed with a sample of fluid known to contain the target enzyme and incubated for a period requisite to allow binding of target enzyme to the ligand. The particles containing enzyme-ligand reaction products bound thereto are then separated from the fluid sample by known separation techniques, including filtration, sedimentation, centrifugation and in the case of superparamagnetic particles, subjection to the influence of a gradient magnetic field of sufficient strength.

The collected particles containing bound enzyme-ligand reaction product, after separation from the initial sample, are then suspended in a volume of known buffer selected as one known to be appropriate to the enzyme-ligand reaction product and this buffer suspension is utilized as the sample in an enzyme-driven test assay constructed for determination of enzyme concentration or some other parameter of the enzyme. This approach is of special value in a method for beta-lactamase enrichment and detection, wherein all beta-lactamase present in a bacterial culture or in sample of human fluid, such as a nasal wash, or a urine sample, is preconcentrated by immunological separation via ligand-bound particles and is then transferred into the uptake volume of the enzyme-driven test.

For convenience of shipping, storage and use, each chromatographic strip of this invention is preferably housed within a suitable device constructed so that the strip is positioned laterally. Many such devices are well-known in the art and any of them constructed so that the performance of an assay on the chromatographic strip positioned within it is performed by lateral flow may appropriately be utilized.

This format for conducting enzyme-driven assays has a number of advantages as hereinafter described in detail.

A specific G6PD assay that can easily be used successfully by anyone operating in the field, the home, a doctor's office or at any site where trained laboratory personnel and instrumentation are lacking, is specifically described hereinafter and depicted in the accompanying drawings, as are assays for total serum cholesterol, beta-lactamase activity, and peroxidase activity.

One aspect of the present invention relates to a chromatographic strip adapted to the performance of a pre-selected enzyme-driven assay for a selected analyte, which strip is (a) adapted to be placed laterally in a supporting device, ensuring lateral flow along its length (b) constructed from a material that permits lateral chromatographic flow through its interstices, and (c) comprises at least two pads sequentially positioned on an adhesive backing, namely, (1) a sample receiving pad adapted to receive a liquid sample which flows laterally and chromatographically therethrough and (2) a substrate pad on which has been movably deposited within an area near its interface with the preceding pad a dry mixture of components that have heretofore been utilized in wet chemistry assays for the same analyte.

In certain embodiments the chromatographic strip comprises a sample receiving pad which is adapted to permit the addition of a lysing agent to a liquid blood sample introduced thereto, and to allow said lysed blood sample to flow chromatographically, in a lateral manner, into the second such pad.

In certain embodiments, the chromatographic strip comprises a region of the first pad which has been pretreated to remove from, or reduce the concentration in the liquid sample as it flows therethrough of a substance known to interfere with, obscure the result of or otherwise hinder the performance of the intended assay if present therein.

In certain embodiments, the chromatographic strip comprises a region of said first pad which has been treated to concentrate the liquid sample as it flows there through by removing a portion of its liquid content.

In certain embodiments, the chromatographic strip comprises an intermediate pad which is interposed between the sample receiving pad and the pad and said intermediate pad has been treated with an immovable deposit of at least one substance that removes and binds at least one sample component that would otherwise interfere with or obscure the result of the assay.

In certain embodiments, the chromatographic strip comprises a substrate pad of which contains dry components that, when reconstituted by chromatographic lateral forward flow with a liquid sample of fresh human blood, perform an enzyme driven assay for G6PD activity on said sample.

Another aspect of the invention relates to a chromatographic lateral flow assay for G6PD activity in human blood comprising the steps of a) applying to the sample receiving end of a laterally positioned chromatographic strip comprising at least two abutting pads positioned on an adhesive strip, each constructed from a material that permits lateral chromatographic flow therethrough, a liquid sample of fresh human blood, b) applying to the sample a lysing agent to split open the red blood cells thereof, c) allowing the lysed blood sample to flow along said strip, into said the second pad, where the momentum of its forward flow picks up a movable predeposited dry substrate mixture containing dry components heretofore utilized in wet chemistry clinical assays for G6PD activity, d) allowing the lysed blood sample containing the dry substrate components in its forward flow front to flow together along said strip to the terminal end thereof, and e) when the lysed blood sample and the dried substrate components reach the terminal end of said strip, noting the appearance of a distinct purplish blue color in the forward flow front due to the formation of formazan.

In certain embodiments, the chromatographic lateral flow assay comprises in step (e) the time required for development of purplish blue color after the sample and reconstituted substrate reach the end of the strip is measured and a determination is made, based upon the measured time and the ambient temperature during performance of the assay, of whether the person from whom the blood sample was obtained has normal or subnormal G6PD activity, based on known time-temperature relationships to G6PD activity levels.

In certain embodiments, the chromatographic lateral flow assay is performed at ambient temperature of approximately 37° C., wherein step (e) is permitted to proceed for 70 seconds from the time the sample and reconstituted substrate reach the terminal end of the chromatographic strip and if no purplish blue color has yet formed, the individual whose blood sample was assayed is classified has having G6PD activity deficiency, but if such color forms before the 70 second limit, the individual whose blood sample was assayed is classified as having normal G6PD activity.

Another aspect of the invention relates to a chromatographic lateral flow assay for a preselected analyte that is enzyme driven and performed (a) by applying to the sample receiving end of a laterally positioned chromatographic strip comprising at least two pads positioned in abutting relationship on an adhesive backing, a liquid sample; (b) allowing said sample to flow through the first pad and into the second pad, where the forward flow momentum of the sample picks up and carries with it to the opposite end of said pad a mixture of dry components which have been utilized in performing wet chemistry assays for the preselected analyte and (c) whereby the dry components are reconstituted by contact with the liquid sample and a color indicative of the endpoint of the assay forms at the flow front position.

In certain embodiments, the chromatographic lateral flow assay for measuring total serum cholesterol in mammalian blood, which strip has a substrate pad on which has been movably deposited within an area near its interface with the preceding pad a dry mixture of components that have heretofore been utilized in wet chemistry assays for total serum cholesterol and a dye forming ingredient.

In certain embodiments, the chromatographic lateral flow for the measurement β-lactamase activity in bacteria cultures, which strip has a substrate pad on which has been movably deposited within an area near its interface with the preceding pad a dry mixture of components heretofore utilized in wet chemistry assays for beta-lactamase activity and a dye-forming ingredient.

In certain embodiments, the chromatographic lateral flow assay for measuring peroxidase activity in human serum or whole blood comprises a strip having a substrate pad on which has been movably deposited within an area near its interface with the preceding pad a dry mixture of components previously utilized in wet chemistry assays for peroxidase activity, plus a dye forming ingredient and sodium nitrite in sufficient quantity to eliminate pseudoperoxidase activity.

Another aspect of the invention relates to a process for performing a preselected enzyme-driven assay for a selected analyte wherein the enzyme generally occurs in very small concentrations in milieus where it is known to be present, which process comprises the steps of (a) adding to a milieu in which the said enzyme is known to occur sufficient aqueous-based liquid to provide a medium within which migration of said enzyme and/or particulate support material impregnated with or conjugated to, a ligand for said enzyme can take place, (b) adding to said medium an increment of particulate support materials of a size larger than any naturally occurring particles that may be present in said medium, which particulate support materials have been conjugated to or impregnated with a ligand for said enzymes, (c) allowing said particulate support materials which have been conjugated or impregnated with a ligand for said enzyme and said enzyme to incubate for a time sufficient to enable said enzyme to react with said ligand conjugated to or impregnated with said particulate support materials under conditions which are conducive to promoting contact between said enzyme and said ligand, (d) recovering from said medium said particulate support materials upon which ligand-enzyme conjugates have formed, (e) dispersing said particulate support materials upon which ligand enzyme conjugates have formed that were recovered in step (d) hereof in a volume of aqueous based medium of requisite sample size for conducting an assay, on a chromatographic strip adapted to the performance of an assay driven by the enzyme present in said ligand-enzyme conjugates, (f) applying said volume of aqueous based medium containing said particulate support material upon which ligand-enzyme conjugates have formed to the sample pad of a chromatographic strip of the present invention that is adapted to the performance of an assay driven by the enzyme present in said ligand-enzyme conjugates, (g) allowing the assay to proceed and (h) reading its results using predetermined color standards.

In certain embodiments, the process for performing a preselected enzyme-driven assay wherein the particulate support material is a porous paper or plastic material and step (d) is performed by filtering out said particulate support materials upon which ligand-enzyme conjugates have formed.

In certain embodiments, the process for performing a preselected enzyme-driven assay wherein the particulate support material is a porous paper or plastic material and step (d) is performed by centrifuging said medium, separating out the layer in which said particulate support materials upon which ligand-enzyme conjugates have formed and aspirating or filtering off any liquid that is present in said layer.

In certain embodiments, the process for performing a preselected enzyme-driven assay wherein the particulate support material is a porous paper or plastic material and step (d) is performed by allowing said medium containing said particulate support materials upon which ligand-enzyme conjugates have formed to rest and separate into layers by natural sedimentation, followed by separating out the layer containing said particulate support materials upon which ligand-enzyme conjugates have formed and removing any liquid present therein by aspiration or filtration.

In certain embodiments, the process for performing a preselected enzyme-driven assay wherein the particulate support material is superparamagnetic particles and step (d) is performed by exposing said medium to the action of a magnetic field of sufficient strength to draw to it the particles on which ligand-enzyme conjugates have formed, the medium is removed by decantation or aspiration, and the isolated particles are released from the magnet and immediately subjected to step (e).

In certain embodiments, the process for performing a preselected enzyme-driven assay wherein the magnet is a rare earth magnet.

In certain embodiments, the chromatographic strip comprises an intermediate pad which is interposed between the sample receiving pad and the substrate pad, said intermediate pad has been treated with an immovable deposit of at least one substance that removes and binds at least one sample component that would otherwise interfere with or obscure the result of the assay.

BRIEF DESCRIPTIONS OF THE DRAWINGS

FIG. 1A represents a chromatographic strip preprepared for the performance of the G6PD assay of this invention.

FIG. 1B shows the same strip after the sample has been applied to it and before the sample has reached the endpoint zone.

FIG. 1C shows the strip as it appears when the assay is completed.

FIG. 2A is a chart showing data obtained from use of the G6PD test of this invention.

FIG. 2B is a graph of time in seconds elapsed from the cessation of forward flow at the end of the strip to the appearance of purplish blue color in the endpoint zone, plotted against G6PD activity level for the samples, measured activity level of which is shown in the FIG. 2A chart.

FIG. 3A is a chart showing data obtained in the test of this invention for total serum cholesterol.

FIG. 3B A plot of time in seconds elapsed from cessation of forward flow at the end of the strip to appearance of blue/purple color in the "read" or endpoint zone, versus total serum cholesterol in mg./deciliter.

FIG. 4A is a chart showing data obtained with whole blood in the total serum cholesterol test, as described in Example 2 hereof.

FIG. 4B is a plot of time in seconds to appearance of bluish purple color against cholesterol in mg. per dl.

FIG. 5A is a chart of data obtained using strips of this invention in measuring-lactamase activity, using commercially available β-lactamase standards.

FIG. 5B is a plot of time in seconds to appearance of bluish purple color against standard activity in U/ml, where "U" represents units of activity.

FIG. 6A is a chart obtained from measuring β-lactamase activity in a culture of *E. coli* known to produce β-lactamase.

FIG. 6B is a graph of the data from FIG. 6A showing time in seconds to appearance of bluish purple color against β-lactamase activity measured in CFU (colony-forming units) per ml.

FIG. 7 is a chart of the data from the measurement of peroxidase as described in Example 4, infra.

DETAILED DESCRIPTION OF THE INVENTION

For purposes of describing this invention in its broadest scope, the following four definitions apply wherever the terms appear in this application:

(1). "Sample" refers to any liquid biological or environmental matrix or any liquid extract or liquid concentrate thereof that is to be assayed.

(2). "Analyte" refers to a target substance of the assay which may be present in, or absent from, the sample. The analyte may itself be an enzyme or it may be a substance required to elicit specific enzyme activities, such as substrate, co-substrate or cofactor.

(3). "Substrate" refers to a combination of those components necessary to elicit a specific enzyme reaction, which components are not present in the sample or are present therein in insufficient quantity where the analyte is not an enzyme, or where the initial enzyme reaction drives a cascade of additional reactions requisite to the desired final determination. The substrate may contain any combination of cofactors, substrates as defined in the preceding sentence, co-substrates, dye or colorimetric components, or enzymes themselves.

(4). The term "dry-chemistry" refers to an assay format where the components required for a given determination on a sample are maintained in dry form until reconstituted by the performance of the assay itself, rather than being reconstituted prior to and separate from the assay procedures.

Reconstituting substrate components necessary in enzyme-driven assays by lateral flow chromatography exhibits a host of advantages in comparison to methods that do not utilize such chromatography. At least some of them are identified below:

In the usual manual performance of enzyme driven assays, it is necessary to dilute the sample serially in order to control rapid enzyme kinetics; in the lateral flow assays of this invention, sample dilution is unnecessary because only a very small sample is applied to the chromatographic strip upon which the assay is performed.

The sample itself reconstitutes the substrate, thereby eliminating the need for separate reconstitution buffers and steps.

This chromatographic reconstitution of the substrate increases the substrate concentration available to the sample over that provided in the usual laboratory performance of a comparable assay.

The chromatographic media utilized are any of those well-known and well-characterized in the art. Their known characteristics may readily be taken advantage of, in particular assays where this is desirable, by reserving a zone of the strip in which to concentrate analyte by removing some of the fluid present therein or by reserving a zone of the strip and pretreating it appropriately so that substances present in the sample that tend to inhibit or interfere with the desired enzyme reaction are wholly or partially immobilized in that zone, or their flowability is retarded there.

Also, inasmuch as the endpoint color formation is restricted to a single endpoint zone, it is much easier to read and evaluate, even without instruments such a spectrophotometers, than when color is diffused throughout a large liquid volume.

Further, the action of the sample in picking up dried substrate at its fluid front results in leaving an essentially substrate free zone immediately adjacent to the endpoint zone. As the sample moves forward, there is clear differentiation between any residual color from hemoglobin and the desired endpoint color, forming at the fluid front. This eliminates any need, in some cases, to remove any substance in the sample (such as the red of hemoglobin) that is known to produce visually obscuring color when manual chemistry tests with liquid samples are performed.

Still further, the relative speed from sample introduction to endpoint reaction that characterizes chromatographic lateral flow tests provides great advantages in the enzyme driven tests. These tests, when conducted by classical manual analytical methods often require digestion times for contact between sample and substrate that are in the order of 30-45 minutes and even longer. Notably, these times do not include the time needed in these classical manual methods for making dilutions, conducting concentration steps or substance removal steps, and the like manipulations. By contrast, the lateral flow assays can usually be conducted in time periods within a 5-20 minute range, starting from the introduction of the sample to the strip and ending with evaluation of the endpoint result.

To measure an analyte in red blood cells, such as the G6PD analyte of Example 1 herein, the red blood cells must be lysed (split open) with surfactants or other lysing agents before the analyte can be measured. Another such analyte normally found in red blood cells, an assay for measuring which in the dry chemistry format of this invention can readily be devised, is pyruvate kinase.

There are also many instances where the analyte is normally present in blood serum or plasma, rather than red blood cells, that are enzyme-driven and may beneficially be converted to the "dry chemistry" format of this invention. Among them are such tests as those for glucose, cholesterol, HDL-cholesterol, triglycerides, urea nitrogen, creatinine, alanine aminotransferase (ALT), aspartate aminotransferase (AST), lactate dehydrogenase (LDH), creatinine kinase (CK) and the like.

The present invention will likewise be useful in instances where the analyte is present in other biological fluids, such as measuring alcohol in saliva or measuring drugs such as acetaminophen or salicylate in urine.

Overall, the present invention is perceived as having special utility in situations where:

(A). the typical concentration of analyte in the sample is very low such as in the creatinine and uric acid test for measuring kidney function; where the intimate mixture of sample and substrate at the fluid front will improve the sensitivity of the test compared to that of classical manual methods;

(B). screen testing providing a qualitative "yes" or "no" result is conducted to determine the onset or severity of a disease, such as the ALT (alanine aminotransferase) and AST (aspartate aminotransferase) screens for liver damage, especially on patients who are taking drugs capable of causing liver damage, and screens conducted on infants for genetically caused disorders, such as the test for phenylketonuria (PKU) or the test for galactose used to detect galactosemia; and the like; and (C). tests where some portion of a sample needs to be removed prior to measurement of another portion—e.g. the measurement of HDL (high density lipids)-cholesterol, wherein LDL (low density lipids) and VLDL (very low density lipids) need to be removed, by precipitation or otherwise, before total HDL-cholesterol is measured.

As is apparent from the foregoing, the invention is adaptable to both qualitative and quantitative formats. Some other milieus, in addition to those mentioned above, in which it is amenable to being widely applied are those wherein enzyme-labeled antibodies have been used in wet chemistry methods, to detect the presence of a suspected antigen in an unknown sample, followed by reacting enzyme-tagged antibody-antigen reaction product with an appropriate color-producing agent. These tests have been traditionally performed both qualitatively and quantitatively in wet chemistry formats. Adapting them to being performed according to this invention will produce all the benefits of speed, ease of manipulation, and the like that are noted hereinfore other enzyme-driven reactions.

Particular attention has been given to date to the application of this invention to whole blood chemistry tests.

For example, glucose may be determined by a reductive assay often utilized in blood taken from diabetic patients. To perform this assay according to the present invention, the immunochromatographic strip is prepared with predeposited dry ingredients consisting of glucose dehydrogenase, nicotinamide adenine dinucleotide ("NAD"), nitro blue tetrazolium and diaphorase. Glucose reduces to its hydride, and the hydride in the presence of diaphorase reduces nitro blue tetrazolium to provide purplish blue color in the "read" zone.

In the oxidative assay for glucose the dry ingredients deposited in the substrate zone are glucose oxidase, peroxidase, 4-aminoantipyrine and phenol, or a derivative of phenol. Glucose and glucose oxidase in the presence of oxygen produce hydrogen peroxide, which in turn reacts with aminopyrine and phenol (or a phenol derivative) to produce a distinct color in the "read" zone.

A cholesterol assay often utilized in performing a blood lipid profile is conducted according to this invention by depositing cholesterol esterase, cholesterol oxidase, 4-amino-antipyrine and a phenol derivative, all in dry form, in the substrate zone. When a blood sample is introduced to the strip, lysed and allowed to flow along the strip, a distinct color is observed in the read zone that has an intensity proportional to the cholesterol concentration in the sample. This permits the development of color standards by well known methods. Such standards are conveniently used in situations where instruments for reading color intensity are not readily available, e.g doctor's offices, the home, in the field, etc.

A test according to this invention for measuring HDL-cholesterol employs a preprepared ICT strip wherein a first zone immediately following the "lyse" zone is provided with deposited, immobilized precipitating reagents that capture and bind the low density ("LDL") and very low density lipids ("VLDL") in the sample, allowing only the HDL-cholesterol in the sample to pass into the substrate zone. The ingredients in the substrate zone are again dry cholesterol esterase, cholesterol oxidase, 4-aminoantipyrine and a phenol derivative and the color produced in the "read" zone is proportional in intensity to the concentration of HDL-cholesterol in the sample.

To perform the creatinine assay for kidney malfunction assessment by the method of this invention, the predeposited dry ingredients in the substrate zone are creatinine immunohydrolase, sarcosine oxidase, peroxidase, 4-aminoantipyrine and a phenol derivative.

An ALT assay for liver malfunction can be performed according to this invention on an ICT strip wherein the dry ingredients predeposited in the substrate zone are pyruvate oxidase, peroxidase, 4-aminoantipyrine and a phenol derivative.

Preparing an ICT strip as herein described with predeposited dry ingredients in the substrate zone consisting of creatinine, adenosine triphosphate, phosphophenol pyruvate, pyruvate oxidase, peroxidase, 4-aminoantipyrine and a phenol derivative enables performance according to this invention of an assay for congestive heart failure.

Where phenylketonuria (PKU) is suspected in neonates, this invention provides a convenient "yes-no" assay wherein an ICT strip is equipped with a dry deposit of phenylalanine dehydrogenase, nicotinamide adenine dinucleotide and diaphorase. When a blood sample is added and color appears in the read zone, the test is positive for PKU; if no color appears, the disease is not present.

Tests for alcohol content in blood can be run both oxidatively and reductively in the method of this invention. A test strip for the reductive test can be prepared by depositing alcohol dehydrogenase, nicotinamide adenine dinucleotide, nitro bluetetrazolium and diaphorase in dry form in the substrate zone; an oxidative test for the same purpose employs an ICT strip in the substrate zone of which is predeposited dry alcohol oxidase, peroxidase, 4-aminoantipyrine and a phenol derivative. In either case, the color in the endpoint, or "read" zone will be proportional to the alcohol content of the blood sample.

An assay for acetaminophen (Tylenol R) in blood can conveniently be run according to this invention. The ICT strip for this purpose will contain predeposited dry aryacylaminidase, ortho-cresol, and an oxidizing agent, such as sodium bisulfite. When a blood sample is added one can determine whether or not the patient has overdosed on the acetaminophen by comparing its color intensity to that of a preestablished color standard.

A rapid dry-chemistry lateral flow assay was devised to illustrate this invention specifically. The detection of G6PD deficiency was selected for this purpose because of the perceived need for a reliable test for this purpose that can be conducted in the field, without instrumentation and in the absence of trained laboratory personnel. Assays for total serum cholesterol, beta lactomase activity and peroxidase activity are also exemplified.

SPECIFIC EXAMPLES

Example 1

This test is performed on a lateral flow strip as pictured in FIG. 1A, having a "lyse" or, wicking, pad from which the sample flows forward into the second, or substrate pad. The latter pad has two regions. The first such region is a tightly confined substrate zone in which is movably pre-deposited all of the dried components that may be conventionally used in the art to enable G6PD in the sample to reduce the faint yellow dye nitroblue tetrazolium, to dark blue formazan. The rate of conversion of nitroblue tetrazolium to dark blue formazan is one of several "wet chemistry" tests that has been used in the art to measure G6PD specific activity. The substrate pad also contains what is initially a substrate-free zone, positioned at the farthest end of the strip from the sample introduction point. As the sample picks up substrate and flows forward the initially substrate-free zone becomes the "read" or endpoint zone when the sample containing reconstituted substrate occupies it and forward flow ceases. Prior to the endpoint zone, as the sample moves along the strip its forward flow momentum picks up the dried substrate components and, as it moves to the end of the strip, reconstitution of the picked up dried ingredients concentrates in the fluid front, which rapidly becomes the endpoint or "read" zone where color develops. The area of the strip just prior to the read zone from which dried substrate has been removed by the fluid front then becomes essentially substrate free, but meanwhile has been colored red by the hemoglobin in the sample that passed through the zone.

A specific advantage of the lateral flow chromatography format for this test over a "wet chemistry" test method is realized because the sample of choice for G6PD activity determinations is blood. This is because, as earlier noted, blood cells contain the vast majority of each human individual's G6PD. The blood cells must be lysed to make the enzyme which codes for G6PD available for the reaction. Lysis i.e. (splitting) of blood cells releases hemoglobin and imparts a red color to the sample which must be removed or at the least, substantially diminished in intensity, when the test is conducted by wet chemistry methods because the blue of formazan is extremely difficult, verging on impossible, to discern visually in a diffuse liquid sample to which a uniform red color has already been imparted. The blue color of formazan in such a diffuse liquid sample can readily be seen, as it emerges, as a mere darkening of the initial red color; moreover, different individuals attempting to see the color change typically interpret any given test differently. In the chromatographic test herein described, however, the red color need not be removed because the reaction of sample and chromatographically reconstituted dried ingredients occurs in a well defined flow region at the fluid front, so that when flow terminates at the end of the chromatographic strip and excess fluid, if any, in the sample runs into a sink, two adjacent regions of the strip are clearly visible. The one closest to the end of the strip, the endpoint or "read" region, is a purplish blue color, while the adjacent region exhibits the red color of hemoglobin and the two are clearly discernable from one another.

In the actual tests performed with the G6PD test device, a human whole blood sample was drawn into a tube containing heparin to prevent clotting of the sample. A portion of the sample was first assayed for G6PD activity using a clinical "wet chemistry" laboratory procedure of the prior art and, by ultraviolet spectrophotometric analysis was confirmed to have a normal human G6PD activity level of 116 U/dl. A portion of the sample was lysed by adding aqueous 10% Triton X-100 in a volume ratio of blood to lysing solution of 10:1. The resulting 10% Triton X-100, 90% whole blood lysate was incubated at 37° C. for 6 hours to allow proteolytic degradation of its initial G6PD activity. Using the same conventional "wet chemistry" laboratory procedure as used on a portion of the whole blood, this sample was found to have no G6PD activity.

A second lysate sample was produced in the same manner as the first. Dilutions of the fresh lysate and the degraded lysate were produced with targeted G6PD activities of 104, 80, 40 and 20 U/dl. The actual activity of each of these samples was measured using the same conventional "wet chemistry" lab procedure. The results of the fresh lysate samples were consistent with the targets established for them, while the degraded samples consistently showed no activity.

To the sample receiving end of each of a series of separately prepared chromatographic G6PD strips mounted laterally on a support there was added 45 µl of each of the fresh and degraded lysate samples. The samples were allowed to flow chromatographically along the laterally placed strips to their terminal ends. As each sample reached the terminal end of a strip, timing was initiated and the time needed for the visible purplish blue color to appear in the endpoint zone was recorded. The activity levels of the fresh lysate samples are shown in the chart that is FIG. 2A. The times to purplish blue color appearance are graphed against enzyme activity level for each fresh lysate sample in FIG. 2B. All concentration levels of the fresh lysate had G6PD activity and eventually produced the purplish blue color in the endpoint or "read" zone of the strip as expected.

These experiments were necessarily performed with pre-lysed blood samples because no G6PD deficient blood samples were available and it was necessary to test a range of G6PD levels to validate the test. Lysis of blood samples at the sample introduction end of a chromatographic strip is a procedure known in the art and is intended to be performed in the known manner on these test strips in actual practice with samples of unknown G6PD activity, thus obviating the need for any pre-test sample treatment. The tests described above were considered necessary for the purpose of establishing a timed endpoint so as to enable users of the test strips in the field to distinguish readily between G6PD deficient blood and G6PD normal blood.

The clinically relevant G6PD deficiency level has heretofore been fixed at 20 U/dl. The assay is designed to be run at ambient temperatures as high as 37° C., which typically occur in warm climates where malaria infections are prevalent and the need to identify G6PD-deficient individuals before prescribing malaria medication is acute. The rate of G6PD enzyme activity at 37° C. is known to be double that at normal room temperature of 25° C. For conducting the G6PD chromatographic test, a target activity level cutoff was set at 50 U/dl at room temperature (corresponding to 25 U/dl at 37° C.). By setting the test endpoint at 70 seconds from the time the sample and entrained reconstituted substrate reach the terminal end of the strip, discrimination between individuals with normal G6PD levels and those whose G6PD levels are clinically deficient can readily be made in the field.

In the regions of the world where malaria is most prevalent, G6PD deficiency is relatively common. The ease of performance of the test by non-laboratory trained personnel and its speed combine to indicate that the use of the lateral flow chromatography G6PD test of this invention will have substantial value in ensuring that malaria-infected G6PD-deficient individuals no longer receive medications for malaria that materially exacerbate their health problems.

Example 2

As previously noted, the measurement of cholesterol concentration in a liquid sample can be performed by the enzyme-driven chromatographic assay of this invention in a manner similar to that for G6PD. A lateral flow test strip was constructed by depositing all of the reagents conventionally used in wet chemistry tests for total serum cholesterol plus a color-producing ingredient required to produce a color change at a rate proportional to the concentration of cholesterol constituents. The phenol derivative used in this experiment was TOOS i.e., 3-(N-ethyl-3-methylanilino)-2-hydroxypropane sulfonic acid (Sigma, E-8631) which produces a blue/purple color that can be readily distinguished above the hemoglobin background of a whole blood sample. A commercially available panel of serum cholesterol standards (Sigma, C-0534) was run on these test strips to confirm that the time to visualization was dependent on cholesterol concentration. A clear dose dependence was observed as seen in FIG. 3A and its plot, FIG. 3B.

To evaluate these test total cholesterol strips with a whole blood sample, a panel of whole blood samples was constructed. Rabbit blood was used to simulate extreme hypocholesterolemia because the rabbit native serum cholesterol level is very low, in this case 38 mg/dl. For the balance of the tests at higher levels, this blood was centrifuged and the serum fraction was withdrawn and separated into aliquots. To each aliquot was added an equal volume of each of the serum cholesterol standards referred to above.

The resulting panel of adjusted whole blood samples was assayed with a commercially available wet chemistry spectrophotometric assay (Thermo Trace, cholesterol concentration from 38 to 328 mg/dl). Each of these adjusted samples was lysed and assayed on a test strip as described above. Again, a clear dose dependence was observed in these whole blood lysate samples. This dependent relationship is apparent from FIG. 4A and the corresponding data plot, FIG. 4B.

In each of FIGS. 3B and 4B, y=cholesterol in mg. per dl. and x=time in seconds to visualization of color in the read zone. The symbol $R^2$ is the correlation coefficient of the data to the curve drawn.

Example 3

The beta-lactams are a class of antibiotics, including penicillins and cephalosporins, which contain a characteristic beta-lactam ring structure. This structure interferes with enzymes needed for the synthesis of peptidoglycan to produce defective cell walls in dividing bacteria and renders these walls susceptible to lysis by osmotic pressure. One mechanism of bacterial resistance to these antibiotics is the production of beta-lactamase enzymes, which specifically cleave the beta lactam ring, rendering the antibiotic ineffective and restoring the ability of the bacteria to multiply successfully.

A lateral flow enzyme-driven chromatographic test strip to detect the presence of β-lactamase was constructed by depositing all of the reagents required according to prescribed prior art wet chemistry methodology, to produce a color change at a rate proportional to the concentration of β-lactamase. As in Example 1, the liquid sample chromatographically reconstitutes the dry ingredients deposited on the chromatographic strip that measure beta lactamase activity, in this example a chromagnic cephalosporin (Oxoid, Sr0112C). Color formation is observed in the reaction zone at the distal end of the strip only if β-lactamase was present in the original sample volume.

To confirm that the time to visualization of color with these strips was dependent on β-lactamase activity, a commercially available purified β-lactamase standard (Sigma, P-4524) was obtained, reconstituted, diluted to a range of β-lactamase activities and run on these test strips. A clear dose dependence was observed as shown in FIG. 5A and its data plot, FIG. 5B.

A sample of *E. coli* bacteria known to produce β-lactamase (ATCC #35218) was obtained and grown by culturing according to the directions accompanying it. The presence of β-lactamase activity in the cultured bacteria was confirmed by a conventional wet chemistry spectrophotometric assay. Next the concentrated culture was diluted, its cell concentration was calculated from a turbidity measurement and a series of dilutions were run on the same test strips for beta-lactamase activity referred to earlier in this example. Here again, a clear dose dependence was observed in these diluted bacterial culture samples. This dependent relationship is apparent from FIG. 6A and its plot, FIG. 6B. In FIGS. 5B and 6B, y represents units of beta-lactamase activity and "Ln" is the natural logarithm of the number "x", which represents the measured time in seconds to visualization of color in the endpoint or read zone. In FIG. 6B, the symbol "E" stands for a factor of 10, while "E" followed by a plus sign and a number signifies 10 to the positive power of the number—e.g., 1.00 E+08 means $1 \times 10^8$. "E" followed by a minus sign and a number means 10 to the negative power of the number—thus in FIG. 6B where "$R^2$=9.955E-01"; "E-01"=$10^{-1}$ and $R^2$ is 0.9955. In both FIGS. 5B and 6B, $R^2$ is the correlation coefficient of the data to the curve drawn.

Current methods of detecting beta lactamase enzymes require that the bacteria suspected of having developed antibiotic immunity be cultured to expand the size of the bacterial colony and consequently expand the amount of β-lactamase present. The colony is then incubated with disks that have been preimpregnated with chromogenic cephalosporins. Each disk absorbs a very small volume of the sample, and any β-lactamase enzyme present cleaves the chromogenic cephalosporin to produce a pronounced color change in the disk.

In an effort to improve accuracy, efficiency and sensitivity of the method, superparamagnetic particles of sufficient magnetic moment to be separated by exposure to the magnetic field of a rate earth magnet are conjugated to antibodies specific to the β-lactamase enzyme. These particles are then added to a large volume of sample from an infected patient whose response to antibiotics is unsatisfactory. In the case of resistant upper respiratory disease, for example, the sample is a nasal wash. When the suspect bacteria are urinary tract pathogens, a urine sample is ideal. The sample and the particles are incubated long enough for reaction to occur. The magnetic particles bearing the enzyme-antibody conjugates are separated by the magnetic field of the rare earth magnet from unreacted particles and the liquid sample. These particles are then released from the magnet and, resuspended in a small volume of buffer compatible with the test reagents on the chromatographic test strip for β-lactamase. Preliminary evaluations of the current practice with chromogenic cephalosporin-impregnated discs and enlarged bacterial colonies obtained by culturing the pathogens from a patient against the efficiencies expected to be realized by the technique described strongly suggest that markedly improved sensitivity will be realized. Moreover, obtaining the information rapidly may in many cases save a patient's life by indicating the need for a quick switch to medication containing no β-lactam.

Example 4

Recent literature, including an article in the New England Journal of Medicine (Prognostic Value of Myeloperoxidase in Patients with Chest Pains: Vol. 349 #17, 1595-1604), highlights the potential importance of Myeloperoxidase as a marker of cardiac disease. As a potential diagnostic tool, a prototype enzyme-driven chromatographic assay was constructed to detect peroxidase activity in either serum or whole blood. A lateral flow test strip was constructed by depositing all of the reagents required in existing wet chemistry methodology to produce a color change at a rate proportional to the peroxidase activity of a test sample.

Briefly, glucose oxidase (Sigma, G-2133), 4-aminoantipyrridine (Sigma, 4382) and the phenol derivative TOOS (Sigma, E-8631) were combined in solution, applied to the sample receiving end of a chromatographic strip and dried. Similarly, a solution of glucose (Sigma, G-7528) was prepared, applied to the distal end of the same strip in a volume such that an empty void space remained between the treated regions and no mixing occurred, and dried. Upon reconstitution of these dried components, as is known in the art, the glucose and glucose oxidase produce hydrogen peroxide which can be utilized by any peroxidase activity in the sample to produce a characteristic purple color from the previously colorless phenol compound.

As hemoglobin, which may be present in small quantities in a serum fraction of whole blood and will be present in large quantities in unseparated whole blood has intrinsic pseudoperoxidase activity, additional reagents were included to insure this activity did not interfere with the tests. Sodium nitrite is a strong oxidizing agent which will rapidly oxidize hemoglobin and eliminate its pseudoperoxidase activity as noted in U.S. Pat. No. 6,200,773. Sodium nitrate (Sigma, S-2252) was added to the first reagent zone of the above described test strip in sufficient quantity to eliminate the pseudoperoxidase activity of a moderately hemolized human serum sample.

To determine whether the time to visualization with these strips was dependent on the peroxidase activity in the test article, a commercially available horseradish peroxidase standard (Sigma, P-8375) was obtained and reconstituted. This standard was then diluted to a range of peroxidase activities in moderately hemolized human serum and run on these test strips. A clear dose dependence in time to visualization was observed as reflected in FIG. 7.

Using the dry chemistry, lateral flow-chromatography format described herein, most enzyme driven tests can readily be rendered easier, faster and cheaper to perform. Combining chromatographic separation techniques such as ion exchange, specific affinity, size exclusion and the like with the dry chemistry, lateral flow test format will in many instances produce even greater benefits.

Those skilled in the art of designing lateral flow chromatography tests will readily perceive ways of applying these techniques to transform much of what is now performed as clinical wet chemistry into low cost, convenient tests performable in virtually any location by almost anyone. In particular, various tests are well known to be performable with alternative dry reagents to those specifically mentioned herein for use the substrate zone. Likewise, the ICT strip may be prepared to enable the performance of additional steps prior to the contact of sample with the dry ingredients in the substrate zone, without departing in any way from the spirit of this invention. It is therefore intended that the present invention be limited only by the appended claims.

We claim:

1. A method of assaying glucose-6-phosphate dehydrogenase (G6PD) in a liquid sample, the method comprising
    (a) applying the sample to a chromatographic strip, the chromatographic strip comprising at least a first pad, a second pad, and an intermediate pad positioned on an adhesive backing, wherein said first pad is a sample receiving pad, which has been treated to concentrate the sample as it flows therethrough by removing a portion of its liquid content, the second pad comprises a mixture of dry components, including a substrate for G6PD, and the intermediate pad is interposed between the sample receiving pad and the substrate pad, wherein the intermediate pad has been treated with an immovable deposit of at least one substance that removes and binds at least one sample component that would otherwise interfere with or obscure the result of the assay for G6PD activity; and
    (b) allowing said sample to flow through the first pad and the intermediate pad, and into the second pad, thereby mobilizing the mixture of dry components,
    whereby the dry components are reconstituted by contact with the liquid sample and a color indicative of the presence or concentration of G6PD is formed at a forward flow front of the chromatographic strip.

2. The method of claim 1, wherein the first pad is a sample receiving pad, wherein a region of the sample receiving pad has been pretreated to remove from, or reduce the concentration in the sample as it flows therethrough of a substance known to interfere with, obscure the result of or otherwise hinder the performance of the assay if present therein.

3. The method of claim 1, wherein the first pad is a sample receiving pad comprising a lysing agent.

4. The method of claim 1, wherein the sample comprises blood, serum, plasma, saliva, urine, nasal wash, or a bacterial culture.

5. The method of claim 1, wherein the sample is obtained from a patient.

\* \* \* \* \*